United States Patent
Larson et al.

(10) Patent No.: US 9,867,658 B2
(45) Date of Patent: *Jan. 16, 2018

(54) KNIFE DEPLOYMENT MECHANISMS FOR SURGICAL FORCEPS

(71) Applicant: COVIDIEN LP, Mansfield, MA (US)

(72) Inventors: Eric R. Larson, Boulder, CO (US); Russell D. Hempstead, Lafayette, CO (US); John J. Kappus, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 204 days.

This patent is subject to a terminal disclaimer.

(21) Appl. No.: 14/795,290

(22) Filed: Jul. 9, 2015

(65) Prior Publication Data

US 2015/0305803 A1 Oct. 29, 2015

Related U.S. Application Data

(63) Continuation of application No. 14/299,740, filed on Jun. 9, 2014, now Pat. No. 9,084,608, which is a (Continued)

(51) Int. Cl.
*A61B 17/285* (2006.01)
*A61B 18/14* (2006.01)
(Continued)

(52) U.S. Cl.
CPC ........ *A61B 18/1445* (2013.01); *A61B 17/295* (2013.01); *A61B 2017/292* (2013.01);
(Continued)

(58) Field of Classification Search
CPC ... A61B 17/29; A61B 17/295; A61B 18/1445; A61B 2017/2926; A61B 2017/2946; A61B 2018/1452; A61B 2018/1455
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN:0007-1447.
(Continued)

*Primary Examiner* — Ryan J Severson

(57) ABSTRACT

A surgical instrument includes an end effector assembly having jaw members movable between spaced-apart, first approximated, and second approximated positions. A knife is selectively movable relative to the end effector assembly between a retracted position, a first extended position, and a second extended position. A trigger is selectively actuatable between a un-actuated position, a first actuated position, and a second actuated position for moving the knife between its respective positions. A control member prevents movement of the trigger when the jaw members are disposed in the spaced-apart position, permits movement of the trigger to the first actuated position but prevents movement beyond the first actuated position when the jaw members are disposed in the first approximated position, and permits movement of the trigger to the second actuated position but prevents movement beyond the second actuated position when the jaw members are disposed in the second approximated position.

18 Claims, 12 Drawing Sheets

Related U.S. Application Data continuation of application No. 13/400,290, filed on Feb. 20, 2012, now Pat. No. 8,747,434.

(51) Int. Cl.
*A61B 17/295* (2006.01)
*A61B 17/29* (2006.01)

(52) U.S. Cl.
CPC ............... *A61B 2017/2925* (2013.01); *A61B 2017/2946* (2013.01); *A61B 2018/1455* (2013.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,496,317 A * | 3/1996 | Goble | A61B 17/29 600/564 |
| 5,573,535 A * | 11/1996 | Viklund | A61B 18/1442 606/37 |
| 5,611,808 A * | 3/1997 | Hossain | A61B 18/1442 606/167 |
| D384,413 S | 9/1997 | Zlock et al. | |
| 5,673,841 A | 10/1997 | Schulze et al. | |
| 5,725,536 A | 3/1998 | Oberlin et al. | |
| 5,735,849 A * | 4/1998 | Baden | A61B 18/1442 606/205 |
| H1745 H | 8/1998 | Paraschac | |
| D402,028 S | 12/1998 | Grimm et al. | |
| D408,018 S | 4/1999 | McNaughton | |
| 5,913,874 A * | 6/1999 | Berns | A61B 17/295 606/205 |
| 5,964,758 A * | 10/1999 | Dresden | A61B 18/1445 606/45 |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| 6,773,434 B2 | 8/2004 | Ciarrocca | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,410,494 B2 * | 8/2008 | Kalmann | A61B 17/29 606/174 |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,766,910 B2 | 8/2010 | Hixson et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,241,282 B2 | 8/2012 | Unger et al. | |
| 8,251,994 B2 | 8/2012 | McKenna et al. | |
| 8,333,765 B2 | 12/2012 | Johnson et al. | |
| 8,454,602 B2 | 6/2013 | Kerr et al. | |
| 8,523,898 B2 | 9/2013 | Bucciaglia et al. | |
| 8,529,566 B2 | 9/2013 | Kappus et al. | |
| 8,568,408 B2 | 10/2013 | Townsend et al. | |
| 8,591,510 B2 | 11/2013 | Allen, IV et al. | |
| 8,603,134 B2 * | 12/2013 | Twomey | A61B 17/2909 606/205 |
| 8,628,557 B2 | 1/2014 | Collings et al. | |
| 8,679,098 B2 | 3/2014 | Hart | |
| 8,679,140 B2 | 3/2014 | Butcher | |
| 8,685,009 B2 | 4/2014 | Chernov et al. | |
| 8,685,056 B2 | 4/2014 | Evans et al. | |
| 8,696,667 B2 | 4/2014 | Guerra et al. | |
| 8,702,737 B2 | 4/2014 | Chojin et al. | |
| 8,702,749 B2 | 4/2014 | Twomey | |
| 8,745,840 B2 | 6/2014 | Hempstead et al. | |
| 8,747,413 B2 | 6/2014 | Dycus | |
| 8,747,434 B2 | 6/2014 | Larson et al. | |
| 8,752,264 B2 | 6/2014 | Ackley et al. | |
| 8,864,795 B2 * | 10/2014 | Kerr | A61B 18/1442 606/167 |
| 9,084,608 B2 | 7/2015 | Larson et al. | |
| 9,186,165 B2 * | 11/2015 | Twomey | A61B 17/2909 |
| 9,192,432 B2 * | 11/2015 | Larson | A61B 18/1445 |
| 9,504,519 B2 * | 11/2016 | Kerr | A61B 18/1442 |
| 2003/0018331 A1 | 1/2003 | Dycus et al. | |
| 2005/0113827 A1 | 5/2005 | Dumbauld et al. | |
| 2007/0043352 A1 * | 2/2007 | Garrison | A61B 18/00 606/51 |
| 2007/0043353 A1 | 2/2007 | Dycus et al. | |
| 2007/0062017 A1 | 3/2007 | Dycus et al. | |
| 2007/0179499 A1 * | 8/2007 | Garrison | A61B 18/1445 606/51 |
| 2009/0157074 A1 * | 6/2009 | Livneh | A61B 18/1445 606/37 |
| 2009/0240245 A1 | 9/2009 | Deville et al. | |
| 2010/0145334 A1 | 6/2010 | Olson et al. | |
| 2010/0179545 A1 * | 7/2010 | Twomey | A61B 18/1445 606/51 |
| 2010/0249816 A1 * | 9/2010 | Whitman | A61B 17/07207 606/167 |
| 2010/0280515 A1 | 11/2010 | Hixson et al. | |
| 2011/0009864 A1 | 1/2011 | Bucciaglia et al. | |
| 2012/0022525 A1 | 1/2012 | Dietz et al. | |
| 2012/0083287 A1 | 4/2012 | Artale et al. | |
| 2012/0184988 A1 * | 7/2012 | Twomey | A61B 17/2909 606/205 |
| 2012/0239034 A1 | 9/2012 | Horner et al. | |
| 2012/0253344 A1 | 10/2012 | Dumbauld et al. | |
| 2012/0259331 A1 | 10/2012 | Garrison | |
| 2012/0265241 A1 | 10/2012 | Hart et al. | |
| 2012/0283727 A1 | 11/2012 | Twomey | |
| 2012/0283734 A1 | 11/2012 | Ourada | |
| 2012/0296205 A1 | 11/2012 | Chernov et al. | |
| 2012/0296238 A1 | 11/2012 | Chernov et al. | |
| 2012/0296239 A1 | 11/2012 | Chernov et al. | |
| 2012/0296317 A1 | 11/2012 | Chernov et al. | |
| 2012/0296323 A1 | 11/2012 | Chernov et al. | |

(56) References Cited

U.S. PATENT DOCUMENTS

| | | |
|---|---|---|
| 2012/0296324 A1 | 11/2012 | Chernov et al. |
| 2012/0296333 A1 | 11/2012 | Twomey |
| 2012/0296334 A1 | 11/2012 | Kharin |
| 2012/0296371 A1 | 11/2012 | Kappus et al. |
| 2012/0303025 A1 | 11/2012 | Garrison |
| 2012/0303026 A1 | 11/2012 | Dycus et al. |
| 2012/0310240 A1 | 12/2012 | Olson et al. |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018371 A1 | 1/2013 | Twomey |
| 2013/0018372 A1 | 1/2013 | Sims et al. |
| 2013/0022495 A1 | 1/2013 | Allen, IV et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072919 A1 | 3/2013 | Allen, IV et al. |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0082035 A1 | 4/2013 | Allen, IV et al. |
| 2013/0085491 A1 | 4/2013 | Twomey et al. |
| 2013/0085496 A1 | 4/2013 | Unger et al. |
| 2013/0085516 A1 | 4/2013 | Kerr et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0150842 A1 | 6/2013 | Nau, Jr. et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0218198 A1* | 8/2013 | Larson ............... A61B 18/1445 606/206 |
| 2013/0226177 A1 | 8/2013 | Brandt et al. |
| 2013/0226178 A1 | 8/2013 | Brandt et al. |
| 2013/0238016 A1 | 9/2013 | Garrison |
| 2013/0245623 A1 | 9/2013 | Twomey |
| 2013/0253489 A1 | 9/2013 | Nau, Jr. et al. |
| 2013/0255063 A1 | 10/2013 | Hart et al. |
| 2013/0274736 A1 | 10/2013 | Garrison |
| 2013/0289561 A1 | 10/2013 | Waaler et al. |
| 2013/0296848 A1 | 11/2013 | Allen, IV et al. |
| 2013/0296856 A1 | 11/2013 | Unger et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0325057 A1 | 12/2013 | Larson et al. |
| 2014/0005663 A1 | 1/2014 | Heard et al. |
| 2014/0005666 A1 | 1/2014 | Moua et al. |
| 2014/0100602 A1* | 4/2014 | Twomey ............ A61B 17/2909 606/208 |
| 2014/0288557 A1* | 9/2014 | Larson ............... A61B 18/1445 606/52 |
| 2015/0066076 A1* | 3/2015 | Kerr ................... A61B 18/1442 606/207 |
| 2015/0305803 A1* | 10/2015 | Larson ............... A61B 18/1445 606/52 |
| 2016/0000496 A1* | 1/2016 | Kerr ................... A61B 18/1442 29/426.2 |
| 2016/0038169 A1* | 2/2016 | Twomey ............ A61B 17/2909 606/206 |
| 2016/0045252 A1* | 2/2016 | Larson ............... A61B 18/1445 606/52 |
| 2017/0071657 A1* | 3/2017 | Kerr ................... A61B 18/1442 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |

(56) References Cited

FOREIGN PATENT DOCUMENTS

| WO | 0059392 A1 | 10/2000 |
|----|------------|---------|
| WO | 0115614 A1 | 3/2001 |
| WO | 0154604 A1 | 8/2001 |
| WO | 02/45589 A2 | 6/2002 |
| WO | 2005/110264 A2 | 11/2005 |
| WO | 2006021269 A1 | 3/2006 |
| WO | 2008040483 A1 | 4/2008 |

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Partial European Search report issued in corresponding application No. 13154180.7 dated Aug. 31, 2017.
Extended European Search Report issued in corresponding European application No. 13154180.7 dated Nov. 24, 2017.

* cited by examiner

KNIFE DEPLOYMENT MECHANISMS FOR SURGICAL FORCEPS

CROSS-REFERENCE TO RELATED APPLICATIONS

This application is a continuation application of U.S. patent application Ser. No. 14/299,740, filed on Jun. 9, 2014, now U.S. Pat. No. 9,084,608, which is a continuation application of U.S. patent application Ser. No. 13/400,290, filed on Feb. 20, 2012, now U.S. Pat. No. 8,747,434, the entire contents of each of which are incorporated herein by reference.

BACKGROUND

Technical Field

The present disclosure relates to surgical instruments and, more particularly, to knife deployment mechanisms for use with surgical forceps for grasping, treating, and/or dividing various tissue structures.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

A surgical instrument provided in accordance with the present disclosure includes an end effector assembly having first and second jaw members. One or both of the jaw members is movable relative to the other between a spaced-apart position, a first approximated position defining a first gap distance therebetween, and a second approximated position defining a second gap distance therebetween. A knife is selectively movable relative to the end effector assembly between a retracted position, a first extended position, in which the knife extends between the jaw members a first distance, and a second extended position, in which the knife extends between the jaw members a second distance. A trigger is selectively actuatable between a un-actuated position, a first actuated position, and a second actuated position for moving the knife between the retracted position, the first extended position, and the second extended position, respectively. One or more control members is operably coupled to the trigger. The control member(s) is configured to prevent movement of the trigger from the un-actuated position when the jaw members are disposed in the spaced-apart position. The control member(s) is further configured to permit movement of the trigger from the un-actuated position to the first actuated position and prevent movement of the trigger beyond the first actuated position when the jaw members are disposed in the first approximated position. The control member(s) is also configured to permit movement of the trigger from the un-actuated position to the second actuated position and prevent movement of the trigger beyond the second actuated position when the jaw members are disposed in the second approximated position.

In one aspect, the surgical instrument includes a drive assembly coupled to one or both of the jaw members. The drive assembly includes a mandrel that is selectively translatable between a first position, a second position, and a third position for moving the jaw members between the spaced-apart position, the first approximated position, and the second approximated position, respectively.

In another aspect, the surgical instrument includes a movable handle coupled to the mandrel. The movable handle is movable between an initial position, a first compressed position, and second compressed position for moving the jaw members between the spaced-apart position, the first approximated position, and the second approximated position, respectively.

In yet another aspect, a first control member is engaged to the mandrel and is movable therewith. In the first position, the first control member interferes with the trigger to prevent actuation of the trigger from the un-actuated position. In the second position, the first control member permits movement of the trigger from the un-actuated position to the first actuated position but interferes with the trigger to prevent actuation of the trigger beyond the first actuated position. In the third position, the first control member permits movement of the trigger from the un-actuated position to the second actuated position but interferes with the trigger to prevent actuation of the trigger beyond the second actuated position.

In still another aspect, a second control member is coupled to the trigger. The second control member is operable to engage the first control member to prevent actuation of the trigger from the un-actuated position when the jaw members are disposed in the spaced-apart position. The second control member is further operable to prevent actuation of the trigger beyond the first actuated position when the jaw members are disposed in the first approximated position. The second control member is also operable to prevent actuation of the trigger beyond the second actuated position when the jaw members are disposed in the second approximated position.

In yet another aspect, the control member includes an elongated body having a plurality of spaced-apart protrusions extending therefrom. The elongated body is movable, upon movement of the mandrel between the first, second, and third positions, between a first blocking position, wherein a first protrusion prevents actuation of the trigger from the un-actuated position, a second blocking position, wherein a second protrusion prevents actuation of the trigger beyond the first actuated position, and a third blocking position, wherein a third protrusion prevents actuation of the trigger beyond the second actuated position.

In still yet another aspect, one or both of the jaw members includes a knife channel defined therein. The knife channel is configured to permit reciprocation of the knife therethrough. More specifically, when the jaw members are disposed in the first approximated position, a relatively smaller portion of the knife is disposed within the knife channel(s) during extension of the knife between the jaw members. On the other hand, when the jaw members are disposed in the second approximated position, a relatively greater portion of the knife is disposed within the knife channel(s) during extension of the knife between the jaw members.

Another surgical instrument provided in accordance with the present disclosure includes an end effector assembly having first and second jaw members. One or both of the jaw members is movable relative to the other between a spaced-apart position, a first approximated position defining a first gap distance therebetween, and a second approximated position defining a second gap distance therebetween. A knife is selectively movable relative to the end effector assembly between a retracted position, a first extended position, in which the knife extends between the jaw members a first distance, and a second extended position, in which the knife extends between the jaw members a second distance. A trigger is selectively actuatable between a un-actuated position, a first actuated position, and a second actuated position for moving the knife between the retracted position, the first extended position, and the second extended position. The trigger has a resistance associated with moving the trigger. One or more control members is operably coupled to the trigger. The control member(s) is configured to provide a first additional resistance to movement of the trigger upon movement of the trigger from the un-actuated position when the jaw members are disposed in the spaced-apart position. The control member(s) is further configured to provide a second additional resistance to movement of the trigger upon movement of the trigger beyond the first actuated position when the jaw members are disposed in the first approximated position. The control member(s) is also configured to provide a third additional resistance to movement of the trigger upon movement of the trigger beyond the second actuated position when the jaw members are disposed in the second approximated position.

In one aspect, the first, second and third additional resistances provide tactile feedback to a user actuating the trigger.

In another aspect, the surgical instrument includes a drive assembly coupled to one or both of the jaw members. The drive assembly includes a mandrel that is selectively translatable between a first position, a second position, and a third position for moving the jaw members between the spaced-apart position, the first approximated position, and the second approximated position, respectively.

In yet another aspect, a first control member is operably coupled to the mandrel and is movable therewith. In the first position, the first control member is positioned to provide the first additional resistance upon movement of the trigger from the un-actuated position. In the second position, the first control member is positioned to provide the second additional resistance upon movement of the trigger beyond the first actuated position. In the third position, the first control member is positioned to provide the third additional resistance upon movement of the trigger beyond the second actuated position.

In still another aspect, a second control member is coupled to the trigger. The second control member is operable to engage the first control member to provide the first additional resistance, the second additional resistance, and the third additional resistance.

In yet another aspect, one or both of the control members is configured to provide audible feedback upon engagement of the first and second control members.

In still yet another aspect, the control member includes an elongated body having a plurality of spaced-apart protrusions extending therefrom. The elongated body is movable, upon movement of the mandrel between the first, second, and third positions, between a first blocking position, wherein a first protrusion provides the first additional resistance to the trigger, a second blocking position, wherein a second protrusion provides the second additional resistance to the trigger, and a third blocking position, wherein a third protrusion provides the third additional resistance to the trigger. One or more of the first, second, and third protrusions may be formed from a resiliently-flexible material.

In another aspect, the surgical instrument includes a movable handle operably coupled to one or both of the jaw members. The movable handle is movable between an initial position, a first compressed position, and second compressed position for moving the jaw members between the spaced-apart position, the first approximated position, and the second approximated position, respectively.

In still yet another aspect, one or both of the jaw members includes a knife channel defined therein. The knife channel is configured to permit reciprocation of the knife therethrough. More specifically, when the jaw members are disposed in the first approximated position, a relatively smaller portion of the knife is disposed within the knife channel(s) during extension of the knife between the jaw members. On the other hand, when the jaw members are disposed in the second approximated position, a relatively greater portion of the knife is disposed within the knife channel(s) during extension of the knife between the jaw members.

BRIEF DESCRIPTION OF THE DRAWINGS

Various aspects of the present disclosure are described herein with reference to the drawings wherein like reference numerals identify similar or identical elements.

DETAILED DESCRIPTION

The operating features and inter-cooperating components of a surgical instrument provided in accordance with the present disclosure are shown in the Figures and described hereinbelow. More specifically, the surgical instrument is shown as a forceps 10, although the present disclosure is equally applicable for use with any surgical instrument having a handle assembly operable to control and/or manipulate an end effector assembly of the surgical instrument and a trigger assembly operable to deploy a knife for cutting tissue grasped by the end effector assembly. Obviously, different connections and considerations apply to each particular type of instrument; however, the novel aspects with respect to the handle assembly, trigger assembly, and the interaction therebetween remain generally consistent regardless of the particular type of instrument used. For the purposes herein, forceps 10 is generally described.

Figure 1:
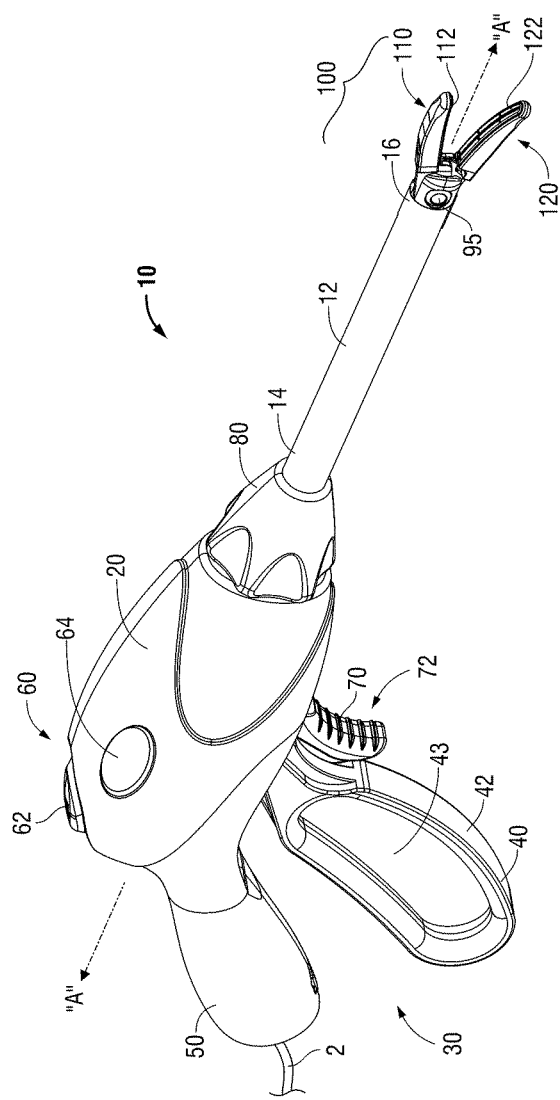
FIG. 1 is a side, perspective view of a forceps provided in accordance with the present disclosure.

Referring to FIG. 1, forceps 10 is configured for use in various surgical procedures and includes a housing 20, a handle assembly 30, a switch assembly 60, a trigger assembly 70, a rotating assembly 80, and an end effector assembly 100 that mutually cooperate to grasp, treat, and divide tubular vessels and vascular tissues. Forceps 10 further includes a shaft 12 having a distal end 16 configured to mechanically engage end effector assembly 100 and a proximal end 14 configured to mechanically engages housing 20. An electrosurgical cable 2 connects forceps 10 to an electrosurgical generator (not shown) such that, upon activation of switch 62 and/or switch 64 of switch assembly 60, energy is supplied to end effector assembly 100 to treat tissue grasped therein, as will be described in greater detail below. Alternatively, forceps 10 may be configured as a battery-powered instrument having a portable battery (not shown) and generator (not shown) disposed within housing 20.

Handle assembly 30 includes a fixed handle 50 and a movable handle 40. Fixed handle 50 is integrally associated with housing 20 and handle 40 is movable relative to fixed handle 50, as will be explained in greater detail below, to impart movement of jaw members 110 and 120 of end effector assembly 100 between a spaced-apart position (FIG. 2A) and one or more approximated positions (FIG. 2B) to grasp tissue therebetween. Rotating assembly 80 is operatively associated with housing 20 and is rotatable about a longitudinal axis "A-A" to rotate end effector assembly 100 about longitudinal axis "A-A." Trigger assembly 70, as will be described in greater detail below, is selectively actuatable to deploy a knife 190 (FIG. 3) from shaft 12 to between jaw members 110, 120 to cut tissue grasped therebetween.

Figure 2A:
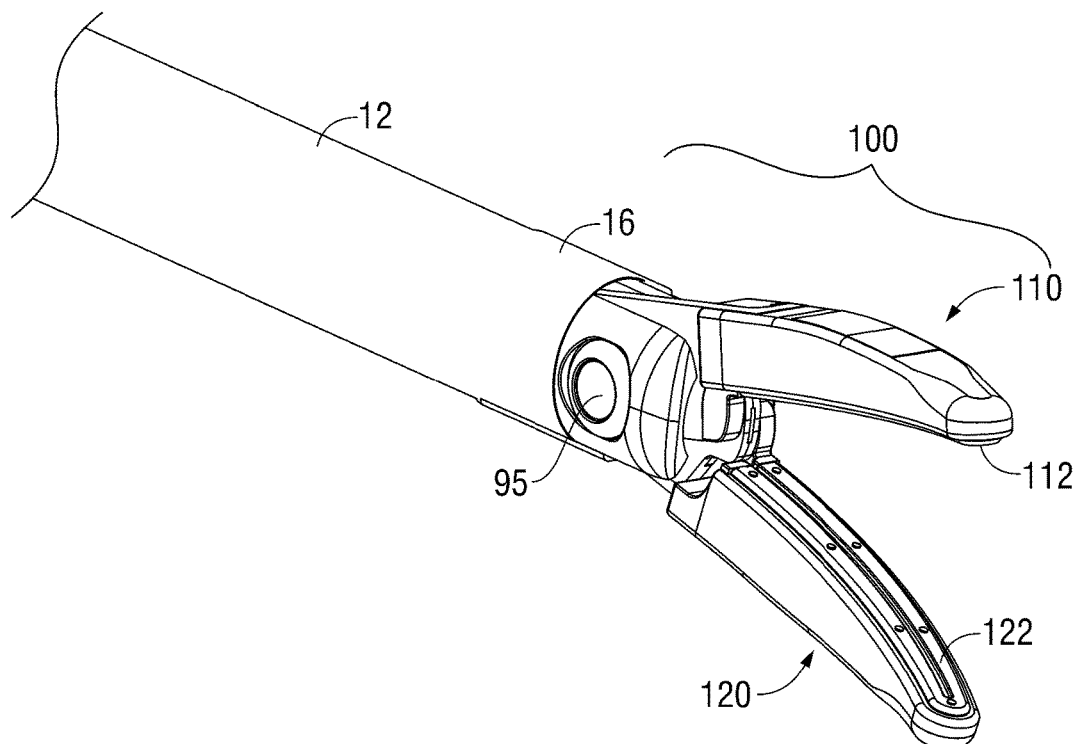
FIG. 2A is a side, perspective view of a distal end of the forceps of FIG. 1 wherein jaw members of the forceps are disposed in a spaced-apart position.
Figure 2B:
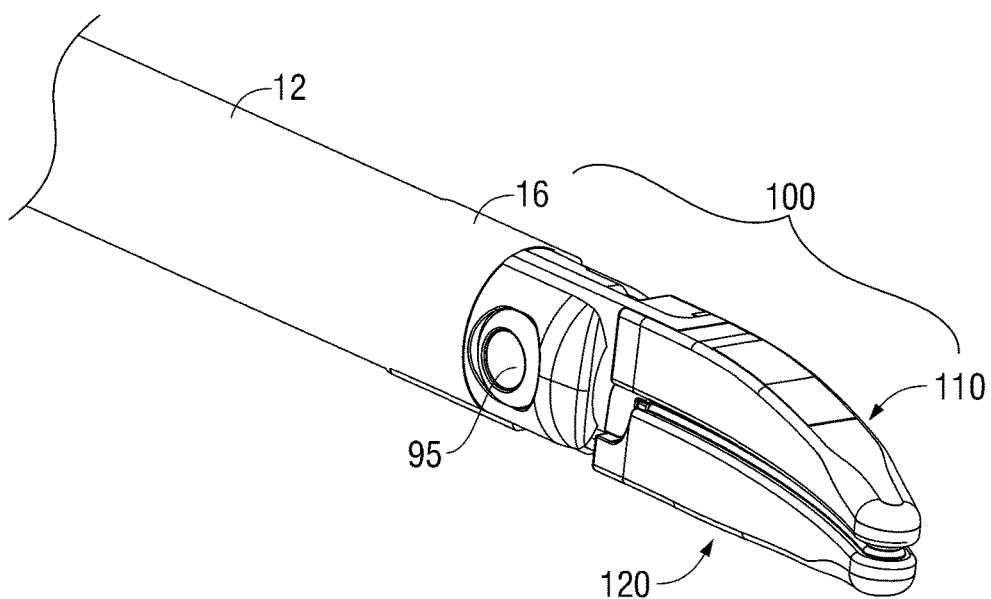
FIG. 2B is a side, perspective view of the distal end of the forceps of FIG. 1 wherein the jaw members of the forceps are disposed in an approximated position.
Figure 3:
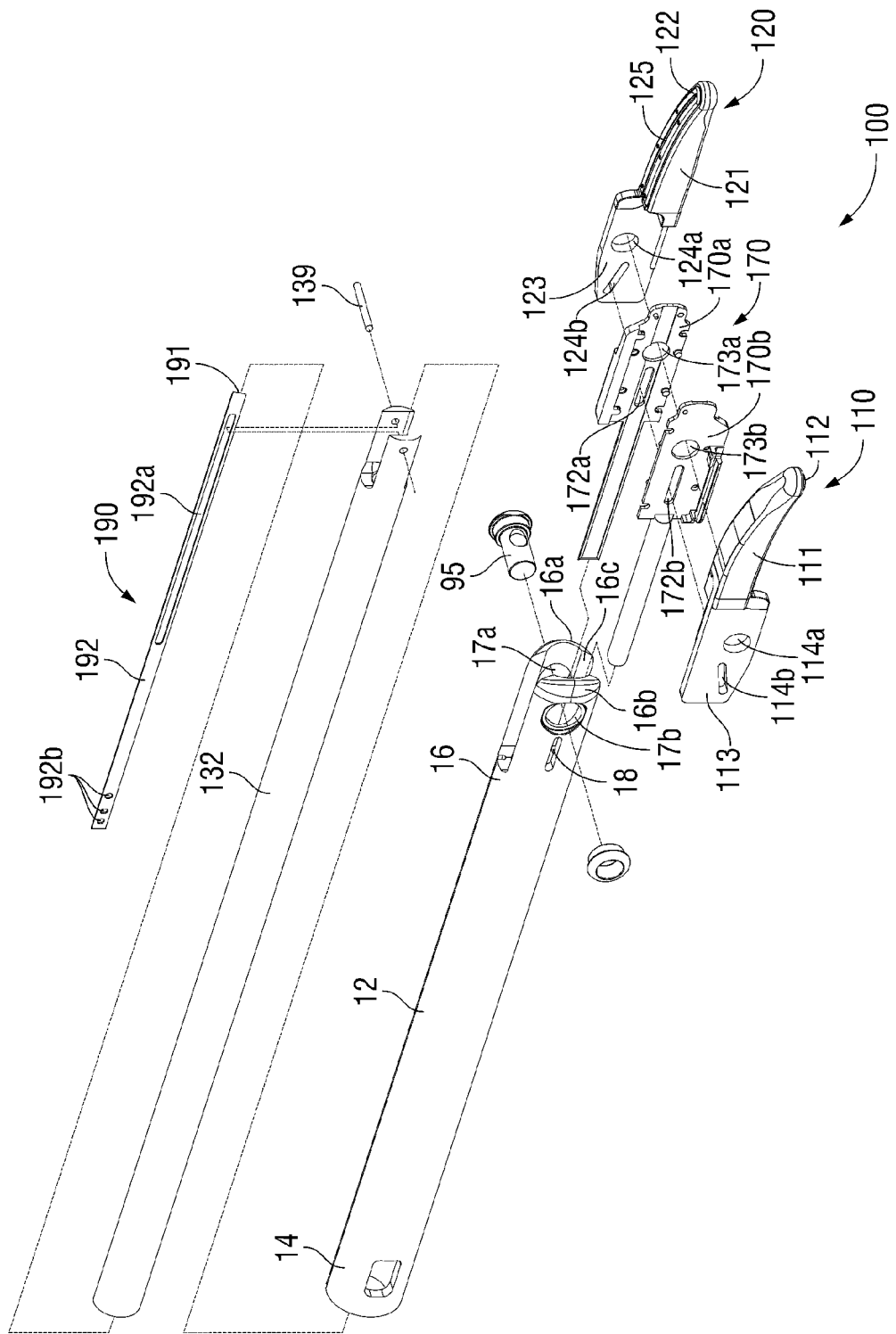
FIG. 3 is a side, perspective view of the distal end of the forceps of FIG. 1 shown with parts separated.

With additional reference to FIGS. 2A-2B and 3, end effector assembly 100 is attached at distal end 16 of shaft 12 and includes a pair of opposing jaw members 110 and 120. End effector assembly 100 is designed as a bilateral assembly, i.e., both jaw members 110 and 120 are movable relative to one another and shaft 12 about a pivot pin 95, although end effector assembly 100 may alternatively be configured as a unilateral end effector assembly. Further, jaw members 110 and 120 of end effector assembly 100 are curved to facilitate manipulation of tissue and to provide better "line of sight" for accessing targeted tissues, although other configurations may also be provided.

With particular reference to FIG. 3, each jaw member 110, 120 includes a distal jaw portion 111, 121 that supports an electrically-conductive tissue sealing plate 112, 122, respectively, thereon, and a proximal flange 113, 123 extending distally from the respective distal jaw portion 111, 121 thereof for operably mounting jaw members 110, 120, respectively, at distal end 16 of shaft 12. Either or both electrically-conductive tissue sealing plates 112, 122 are adapted to connect to a source of energy, e.g., a generator (not shown), for conducting energy therebetween and through tissue grasped between jaw members 110, 120 to treat, e.g., seal, tissue. More specifically, wire(s) (not shown) may extend from electrosurgical cable 2 (FIG. 1), through housing 20 and shaft 12, ultimately connecting to one or both of tissue sealing plates 112, 122, although other configurations are also contemplated. The tissue sealing plates 112, 122 and distal jaw portions 111, 121 of one or both of jaw members 110, 120, respectively, cooperate to define a longitudinally-oriented knife channel 125 therein that is configured to permit reciprocation of a knife 190 therethrough.

Figure 10:
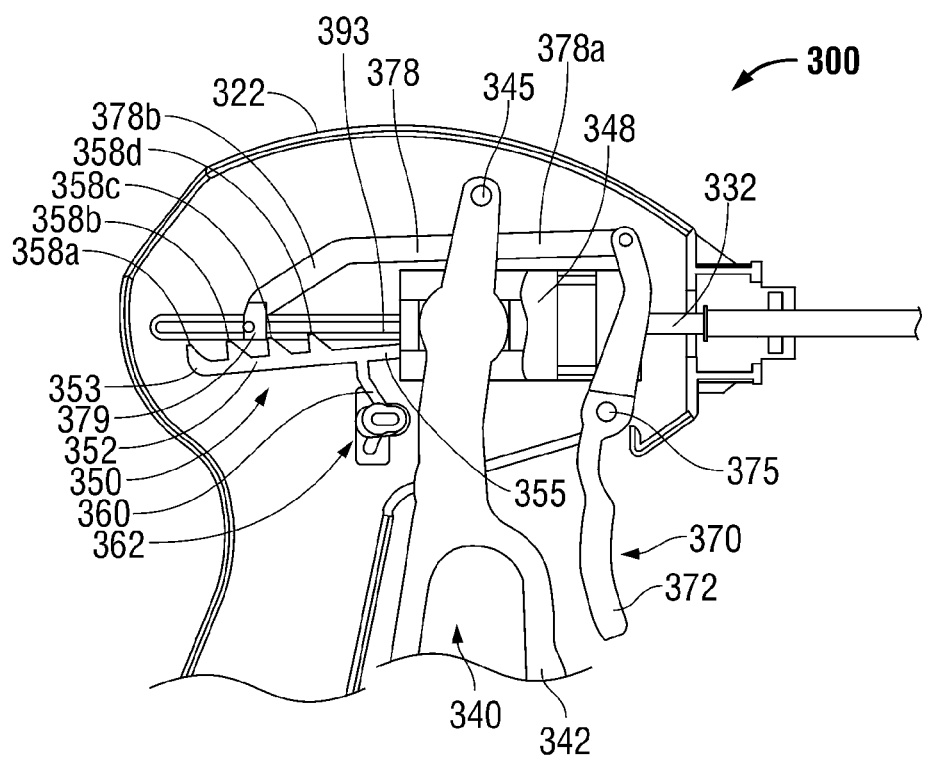
FIG. 10 is a side, cut-away view of the forceps of FIG. 9 wherein the handle assembly is disposed in a compressed position and wherein the trigger assembly is disposed in an actuated position.

Proximal flanges 113, 123 of jaw members 110, 120, respectively, each include a pivot aperture 114a, 124a, respectively, defined therethrough, and an angled cam slot 114b, 124b, respectively, defined therethrough. End effector assembly 100 also includes a knife guide 170 that facilitates alignment and translation of knife 190 through knife channels 125 upon reciprocation of knife drive rod 193 (FIG. 10). Knife guide 170 includes first half 170a and second half 170b which mechanically interface to slidably encapsulate the knife 190 therein. First and second halves 170a and 170b each include an pivot aperture 173a, 173b, respectively, defined therethrough and a longitudinal cam slot 172a, 172b, respectively, defined therethrough. Distal end 16 of shaft 12 includes a bifurcated portion including first and second flanges 16a and 16b, respectively, that define a channel 16c therebetween for receiving jaw members 110 and 120. Each flange 16a, 16b defines a pivot aperture 17a, 17b, respectively, therethrough for receipt of pivot pin 95, and a longitudinal cam slot 18.

During assembly, pivot pin 95 is inserted through pivot aperture 17a of flange 16a of shaft 12, pivot aperture 124a of proximal flange 123 of jaw member 120, pivot aperture 173*a* of first half 170*a* of knife guide 170, pivot aperture 173*b* of second half 170*b* of knife guide 170, pivot aperture 114*a* of proximal flange 113 of jaw member 110, and pivot aperture 17*b* of flange 16*b* of shaft 12 to pivotably engage jaw members 110, 120 at distal end 16 of shaft 12. Angled cam slots 114*b*, 124*b* of jaw members 110, 120, longitudinal cam slots 172*a*, 172*b* of first and second halves 170*a*, 170*b* of knife guide 170, and longitudinal cam slots 18 of flanges 16*a*, 16*b* of shaft 12 are configured to receive drive pin 139, which is engaged to drive sleeve 132 at the distal end thereof. As such, upon translation of drive sleeve 132, drive pin 139 is translated along slots 114*b*, 124*b*, 172*a*, 172*b*, and 18 to pivot jaw members 110, 120 relative to one another between the spaced-apart position (FIG. 2A) and the one or more approximated positions (FIG. 2B).

Knife 190 is configured for reciprocation through shaft 12 and knife channels 125 of jaw members 110, 120, respectively, between a retracted position, wherein knife 190 is positioned proximally of distal jaw portions 111, 121 of jaw members 110, 120, respectively, and one or more extended positions, wherein knife 190 extends at least partially through knife channels 125 of jaw members 110, 120 to cut tissue grasped therebetween. Knife 190 includes a distal blade 191 configured to facilitate cutting tissue upon translation of knife 190 between jaw members 110, 120, and a elongated body portion 192. Body portion 192 of knife 190 defines a longitudinal slot 192*a* extending therethrough that is configured to receive pivot pin 95 and drive pin 139 to permit translation of knife 190 about pivot pin 95 and drive pin 139. The proximal end of knife 190 defines one or more pin holes 192*b* therethrough for engaging knife 190 to knife drive rod 193 (FIGS. 4A-4B), although other engagement configurations are also contemplated. As will be described in greater detail below, knife drive rod 193 (FIGS. 4A-4B) is selectively translatable, e.g., upon actuation of trigger 72 assembly 70 (FIGS. 4A-4B), through shaft 12 and relative to end effector assembly 100 to translate knife 190 between the retracted and the one or more extended positions.

Figure 4A:
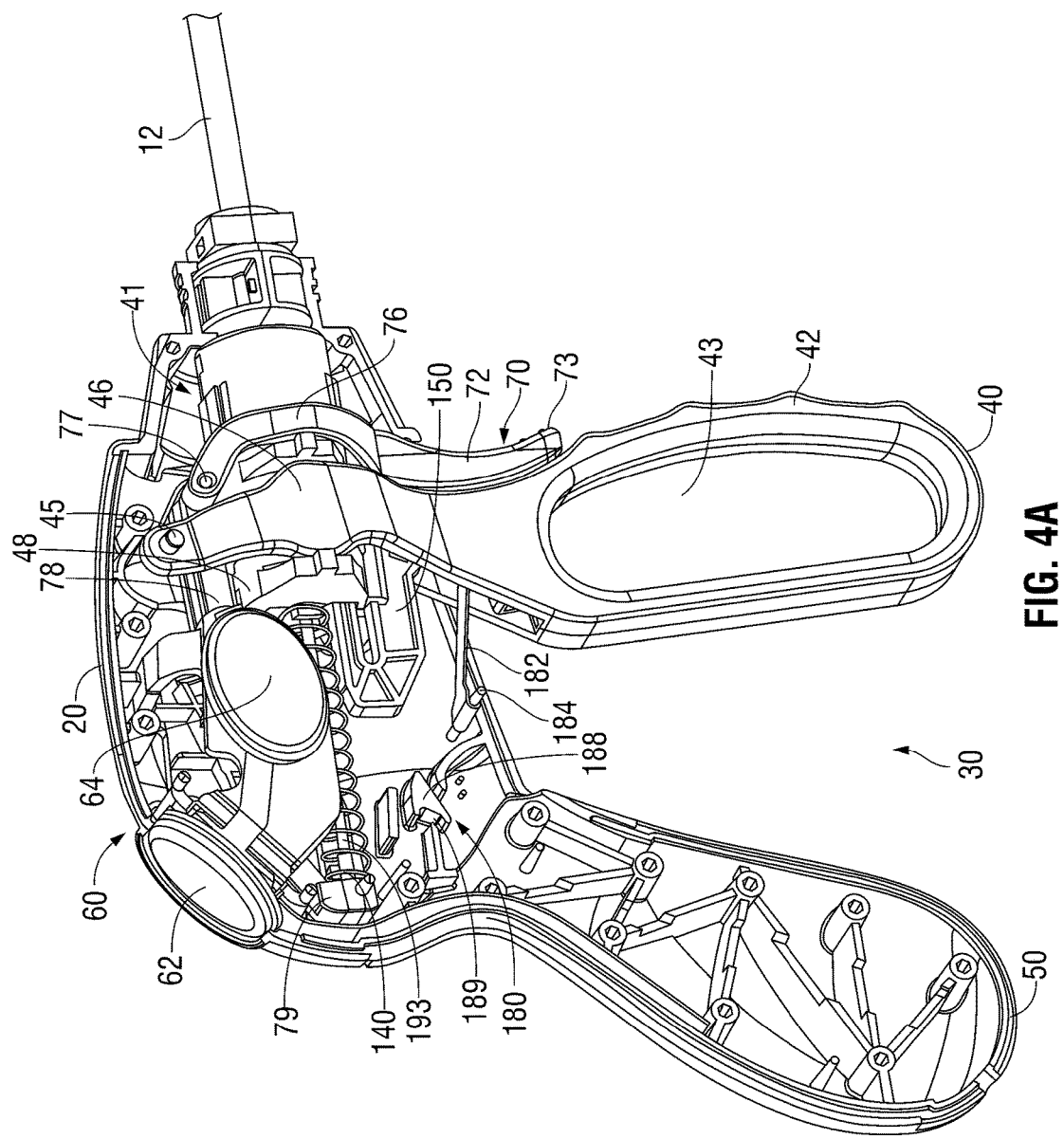
FIG. 4A is a side, perspective view of a proximal end of the forceps of FIG. 1 wherein a portion of a housing has been removed to show the internal components thereof.
Figure 4B:
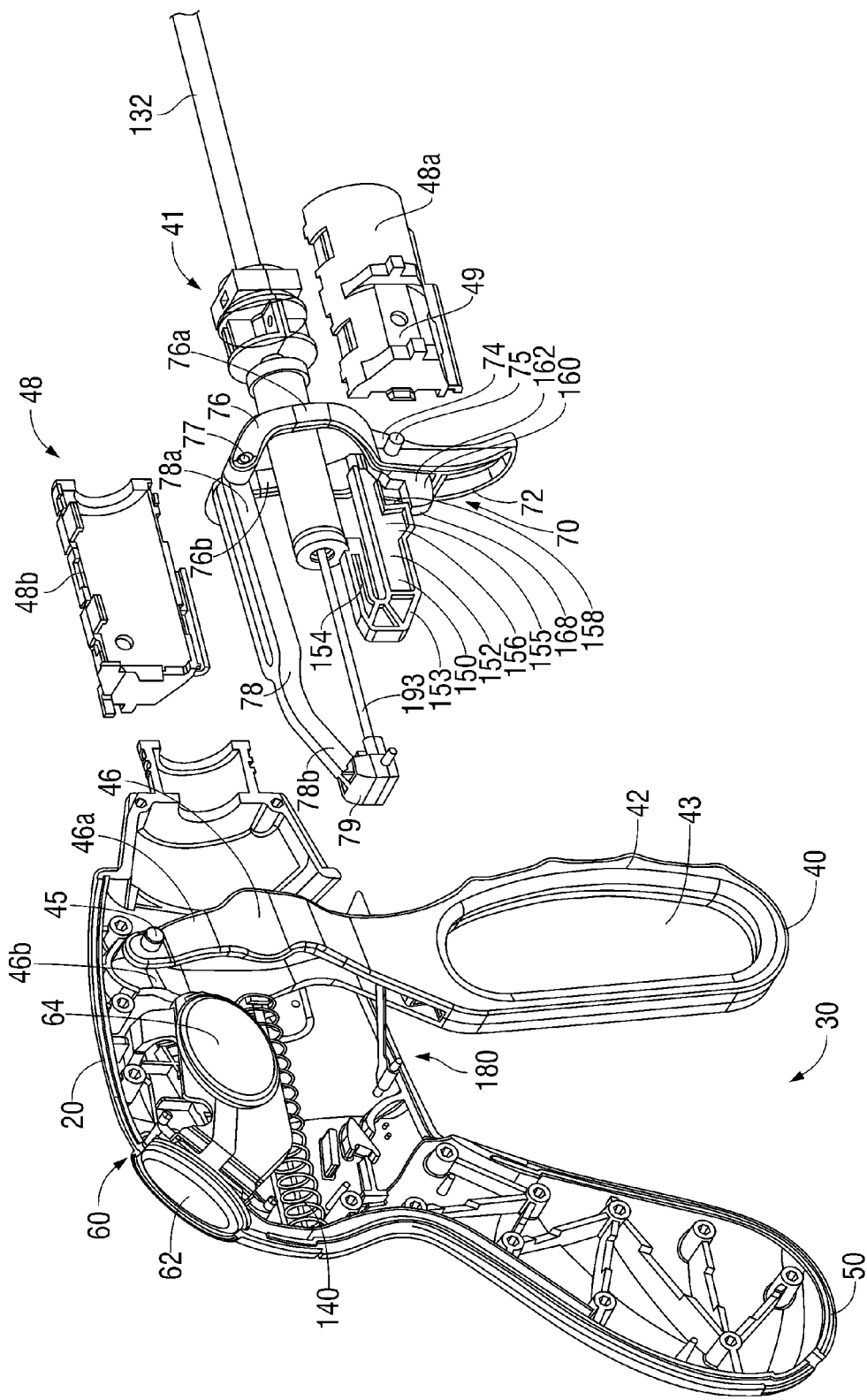
FIG. 4B is a side, perspective view of the proximal end of the forceps of FIG. 1 with a portion of the housing removed with parts separated.

Turning now to FIGS. 4A-4B, in conjunction with FIGS. 1-3, movable handle 40 includes a lever 42 defining a finger hole 43 and a bifurcated arm 46 extending upwardly from lever 42 and into housing 20. Arm 46 is bifurcated to define first and second spaced-apart flanges 46*a*, 46*b*, respectively, that are pivotably coupled to housing 20 at the free ends thereof via pivot pin 45. Flanges 46*a*, 46*b* extend on either side of drive assembly 41 and are coupled thereto to facilitate movement of jaw members 110, 120 between the spaced-apart position and the one or more approximated positions. More specifically, flanges 46*a*, 46*b* extend upwardly on either side of mandrel 48 and are disposed within lateral slots 49 defined within first and second mandrel components 48*a*, 48*b*, respectively. First and second mandrel components 48*a*, 48*b* are engaged to one another about drive sleeve 132, e.g., via snap-fitting or other suitable engagement, to fixedly engage mandrel 48 about drive sleeve 132. Due to this configuration, upon pivoting of movable handle 40 about pivot pin 45 and relative to fixed handle 50 from an initial position (FIG. 4A) to one or more compressed positions (FIG. 6), mandrel 48 and drive sleeve 132 are translated proximally, thereby translating drive pin 132 proximally through angled cam slots 114*b*, 124*b* of jaw members 110, 120, respectively, (and cam slots 18 and 172*a*, 172*b* of shaft 12 and knife guide 170, respectively) to pivot jaw members 110, 120 from the spaced-apart position (FIG. 2A) to the one or more approximated positions (FIG. 2B). On the other hand, return of movable handle 40 towards the initial position returns drive sleeve 132 distally, thereby returning jaw members 110, 120 towards the spaced-apart position. A spring 140 is coupled between housing 20 and the proximal end of mandrel 48 to bias mandrel 48 distally, thereby biasing movable handle 40 towards the initial position and jaw members 110, 120 towards the spaced-apart position. Further, a first control member 150 is engaged to mandrel 48 to, as will be described in greater detail below, selectively control actuation of trigger assembly 70 in accordance with the relative positioning of jaw members 110, 120.

Movable handle 40 further includes a latch assembly 180 extending proximally therefrom. Latch assembly 180 includes a resilient member 182, e.g., a flat spring, having a pin 184 engaged at the free end thereof. Upon movement of movable handle 40 from the initial position to the one or more compressed positions, resilient member 182 is flexed to permit pin 184 to pass over latch member 188 disposed within housing 20. Latch member 188 includes a catch 189 defined therein that is configured to receive pin 184 for retaining, or latching movable handle 40 in one or more of the compressed positions and, thus, jaw members 110, 120 in one or more of the approximated positions grasping tissue therebetween. Latch member 188 may further include incremental catches (not explicitly shown) for latching movable handle 40 at various different positions corresponding to various different approximated positions of jaw members 110, 120, e.g., a first approximated position, wherein jaw members 110, 120 define a first gap distance "G" (FIGS. 6A-6B) therebetween, and a second approximated position, wherein jaw members 110, 120 define a second, smaller gap distance "g" (FIGS. 7A-7B) therebetween. Other latching mechanisms may also be provided.

With continued reference to FIGS. 4A-4B, trigger assembly 70 includes a trigger 72 having a toggle member 73 and a bifurcated arm 76 extending upwardly from toggle member 73 and into housing 20. Trigger 72 is pivotably coupled to housing 20 via pivot pin 75, which extends through an intermediate portion 74 of trigger 72. Arm 76 is bifurcated to define first and second spaced-apart flanges 76*a*, 76*b*, respectively, to permit passage of arm 76 about drive assembly 41. A pin 77 extends between flanges 76*a*, 76*b* at the free ends thereof. A connector rod 78 is pivotably coupled to pin 77 at distal end 78*a* thereof and is engaged to a base 79 at proximal end 78*b* thereof. Base 79, in turn, is engaged to the proximal end of knife drive rod 193, which extends distally therefrom through drive sleeve 132, ultimately engaging the proximal end of knife 190 (FIG. 3). Accordingly, upon pivoting of trigger 72 about pivot pin 75 and relative to housing 20 from an un-actuated position (FIG. 4A) towards one or more actuated positions, flanges 76*a*, 76*b* and pin 77 are rotated to pull connector rod 78 distally such that knife drive rod 193 is pushed distally to thereby translate knife 190 from the retracted position towards the one or more extended positions. On the other hand, upon return of trigger 72 towards the un-actuated position, flanges 76*a*, 76*b* and pin 77 are rotated to push connector rod 78 proximally such that knife drive rod 193 is pulled proximally to thereby translate knife 190 back towards the retracted position. Spring 140, which is disposed about knife drive rod 193 between base 79 and mandrel 48 biases base 79 proximally, thereby biasing trigger 72 towards the un-actuated position and knife 190 towards the retracted position. Further, a second control member 160 is engaged to trigger 72 about pivot pin 75 to, in conjunction with first control member 150 of drive assembly 41, selectively control actuation of trigger assembly 70 in accordance with the relative positioning of jaw members 110, 120, as will be described in greater detail below.

As mentioned above, drive assembly 41 includes a first control member 150 coupled to mandrel 48 and trigger assembly 70 includes a second control member 160 coupled to trigger 72. First control member 150 includes a body 152 defining a proximal end 153 having an attachment member 154 extending therefrom and a distal end 155 having an engagement leg 156 extending therefrom. Attachment member 154 is configured to engage the proximal end of mandrel 48 such that translation of mandrel 48, e.g., upon compression or return of movable handle 40, effects similar translation of first control member 150. Housing 20 may include a track (not explicitly shown) defined therein that is configured to guide translation of first control member 150 relative thereto. Engagement leg 156, which extends distally from body 152 of first control member 150, defines a generally distally-facing angled contact surface 158.

Second control member 160, as mentioned above, is pivotably engaged to trigger 72 about pivot pin 75. Second control member 160 includes a body 162 defining a generally-proximally facing complementary angled contact surface 168 that is angled similarly to angled contact surface 158 of first control member 150. First and second control members 150, 160, respectively, and, more particularly, angled contact surface 158 and complementary angled surface 168, respectively, thereof, cooperate to selectively control actuation of trigger assembly 70 in accordance with the relative positioning of jaw members 110, 120. More specifically, first and second control members 150, 160, respectively, are configured such that deployment of knife 190 is prevented when jaw members 110, 120 are disposed in the spaced-apart position and such that, when jaw members 110, 120 are disposed in the one or more approximated positions, the extent to which knife 190 may be deployed is dependent on the relative spacing between first and second jaw members 110, 120, respectively. For example, when jaw members 110, 120 are disposed in a first approximated position grasping relatively larger-diameter tissue therebetween such that jaw members 110, 120 are spaced-apart a first gap distance "G," trigger 72 may only be actuated so as to translate knife 190 to a first extended position, e.g., the position shown in FIGS. 6 and 6A-6B. On the other hand, when jaw members 110, 120 are disposed in a second approximated position defining a second gap distance "g" therebetween, e.g., where relatively smaller-diameter tissue is grasped therebetween, trigger 72 may be actuated to translate knife 190 to a second extended position, e.g., the position shown in FIGS. 7 and 7A-7B.

Such a feature is advantageous in that the likelihood of knife trap, knife splay, and/or knife mis-alignment is reduced. This is because knife 190 is most vulnerable to knife trap, knife splay, and/or knife mis-alignment when jaw members 110, 120 are spaced-apart a relatively greater distance, e.g., when a relatively smaller portion of knife 190 is disposed within knife channels 125 of jaw members 110, 120 thus leaving a larger portion of knife 190 un-guarded (as compared to when jaw members 110, 120 are closer-together, thus allowing a greater portion of knife 190 to be disposed within and guarded by knife channels 125) and when knife 190 is further extended between jaw members 110, 120 (as compared to when only a small portion of knife 190 extends between jaw members 110, 120). Thus, by regulating the extent to which knife 190 can be deployed as a function of the gap distance between jaw members 110, 120, the most vulnerable situations where knife trap, knife splay, and/or knife mis-alignment may occur, e.g., where only a relatively small portion of knife 190 is disposed within knife channels 125 and where a greater portion of knife 190 is extended between jaw members 110, 120, can be avoided. The cooperating features of first control member 150 of drive assembly 41 and second control member 160 of trigger assembly 70 which interact to regulate deployment of knife 190 will become more apparent below in view of the description of the use and operation of forceps 10.

Figure 5:
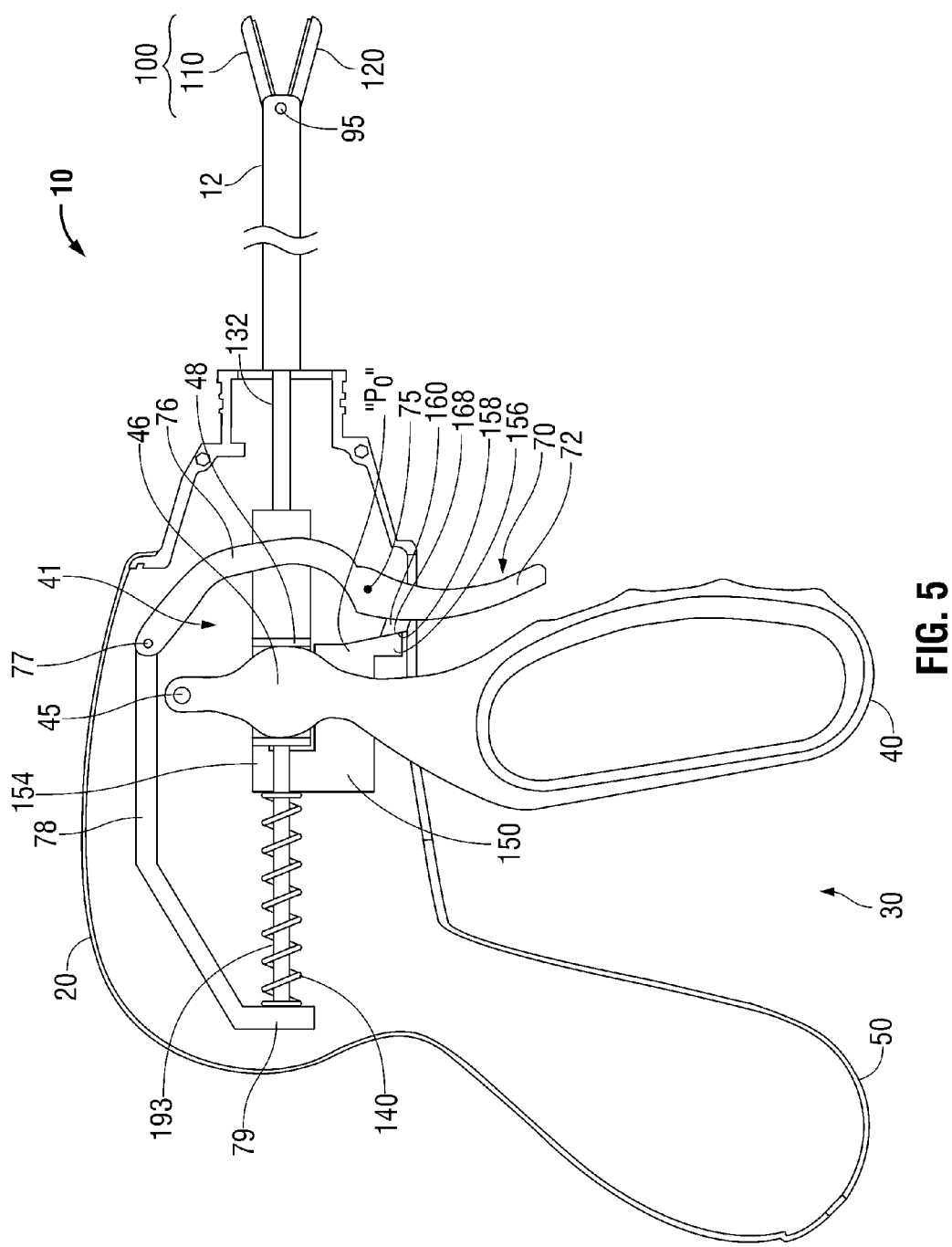
FIG. 5 is a side, cut-away view of the forceps of FIG. 1 wherein a handle assembly is disposed in an initial position, a trigger assembly is disposed in an un-actuated position, and the jaw members are disposed in the spaced-apart position.

The use and operation of forceps 10 for grasping, treating, and/or dividing various different tissues and/or performing various different tissue treatments is described with reference to FIGS. 1-7B. Referring initially to FIG. 5, in conjunction with FIGS. 1-4B, with jaw members 110, 120 disposed in the spaced-apart position, forceps 10 is manipulated and/or maneuvered into position such that tissue to be grasped, treated, and/or divided in disposed between jaw members 110, 120. At this point, movable handle 40 is disposed in the initial position and trigger 72 is disposed in the un-actuated position such that knife 190 is disposed in the retracted position. With movable handle 40 disposed in the initial position, mandrel 48 is positioned is a more-distal position and, thus, first control member 150 is likewise positioned in a more-distal, or initial position "$P_0$." In the initial position of first control member 150, angled surface 158 abuts complementary angled surface 168 of second control member 160 of trigger 72, preventing actuation of trigger 72. As such, knife 190 is maintained in the retracted position when jaw members 110, 120 are disposed in the spaced-apart position.

Figure 6:
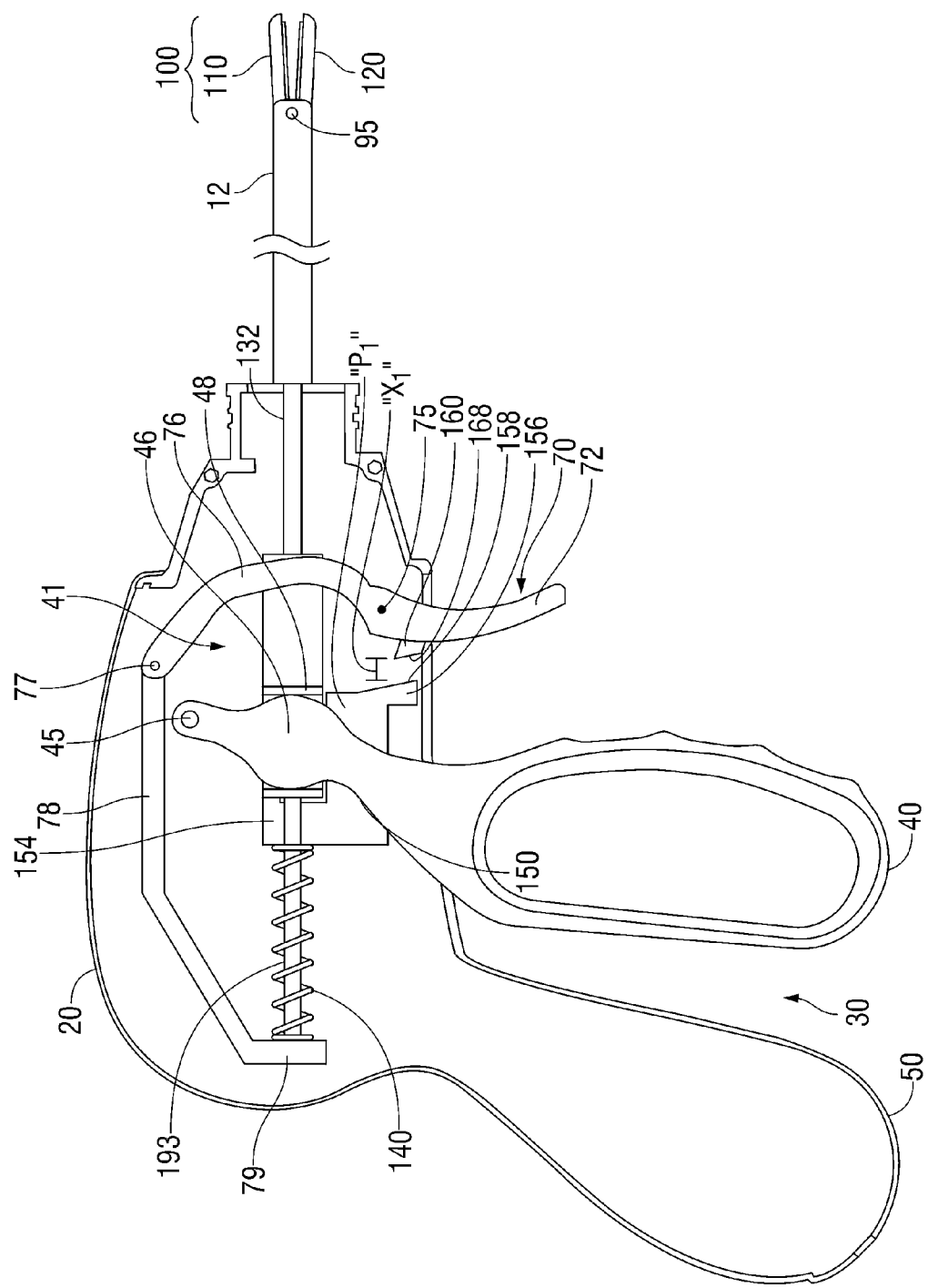
FIG. 6 is a side, cut-away view of the forceps of FIG. 1 wherein the handle assembly is disposed in a first compressed position, the trigger assembly is disposed in an un-actuated position, and the jaw members are disposed in a first approximated position.
Figure 6B:
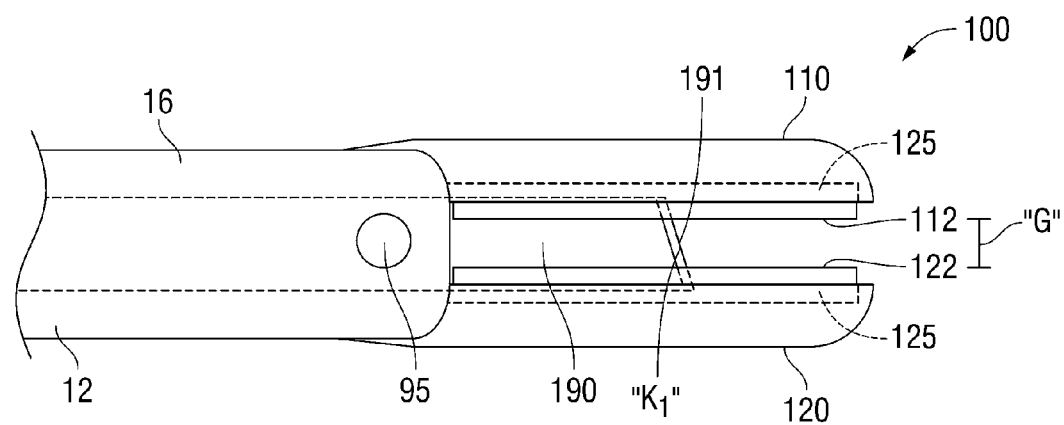
FIG. 6B is a side view of the jaw members of the forceps of FIG. 1 disposed in the first approximated position and including the knife extending partially therebetween.
Figure 6A:
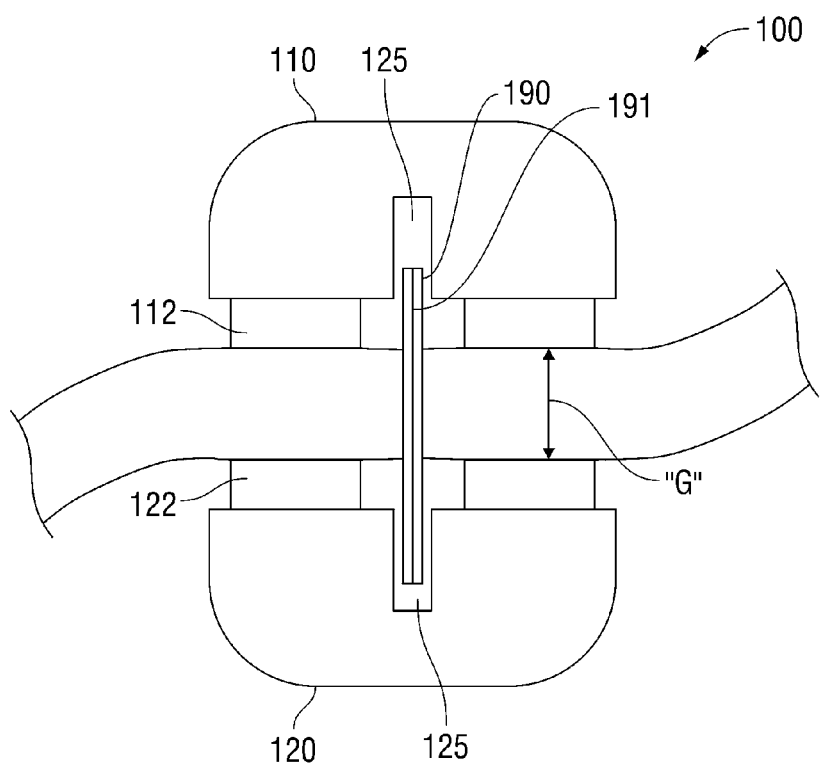
FIG. 6A is a transverse, cross-sectional view of the jaw members of the forceps of FIG. 1 disposed in the first approximated position grasping tissue therebetween, wherein a knife has been advanced between the jaw members to cut tissue grasped therebetween.

With reference now to FIGS. 6 and 6A-6B, in conjunction with FIGS. 1-4B, in order to grasp, treat, and/or divide relatively large-diameter tissue, relatively less compressible tissue, for procedures where a larger gap distance is desired, and/or for procedures where a lesser closure pressure is desired, movable handle 40 is compressed, or pulled proximally relative to fixed handle 50 from the initial position to a first compressed position such that jaw members 110, 120 are pivoted relative to one another to the first approximated position to grasp tissue therebetween. More specifically, as movable handle 40 is compressed, mandrel 48 and drive sleeve 132 are translated proximally, thus pulling jaw members 110, 120 to pivot towards one another to the first approximated position, wherein jaw members 110, 120 define a gap distance "G" therebetween. Jaw members 110, 120 may be approximated to a particular position, e.g., the first approximated position, to achieve a desired closure pressure on tissue, or until a particular latching position is achieved, e.g., via engagement of latch assembly 180 (FIGS. 4A-4B) at a particular position. The proximal translation of mandrel 48 also effects proximal translation of first control member 150 from the initial position "$P_0$" to a first proximal position "$P_1$," wherein first control member 150 is spaced-apart from second control member 160 a distance "$x_1$."

With jaw members 110, 120 grasping tissue between tissue sealing plates 112, 122, respectively, thereof, tissue sealing plate 112 and/or tissue sealing plate 122 may be energized, e.g., via actuation of one or both of switches 62, 64 of switch assembly 60 (FIG. 1), to conduct energy between tissue sealing plates 112, 122 and through tissue to treat, e.g., seal, tissue.

At the completion of tissue treatment, or where it is only desired to cut tissue, trigger 72 may be actuated to cut tissue grasped between jaw members 110, 120. Since first control member 150 is disposed in the first proximal position "$P_1$" a distance "$x_1$" from second control member 160, trigger 72 may be partially actuated, e.g., to translate second control member 160 the distance "$x_1$." More specifically, trigger 72 may be actuated from the un-actuated position to a first actuated position, until complementary angled surface 168 of second control member 160 is moved the distance "$x_1$" to abut angled surface 158 of first control member 150, thereby preventing further actuation of trigger 72. As trigger 72 is actuated, connector rod 78 and knife drive rod 193 are pulled distally, thereby urging knife 190 from the retracted position to the first extended position wherein, as shown in FIG. 6B, knife 190 extends partially between jaw members 110, 120, to position "$k_1$," to cut tissue grasped therebetween. Knife 190 is prevented from further translation through knife channels 125 and between jaw members 110, 120 due to the abutment of angled surface 158 of first control member 150 and complementary angled surface 168 of second control member 160. As mentioned above, this feature protects knife 190 by preventing knife 190 from being further extended in a situation where a relatively smaller portion of knife 190 is disposed within and guided by knife channels 125 of jaw members 110, 120 (due to the relatively larger gap distance "G" between jaw members 110, 120).

Once tissue has been cut, knife 190 is retracted, e.g., via releasing trigger 72 and allowing trigger 72 to return under bias to the un-actuated position. Thereafter, movable handle 40 is unlatched and/or released and is returned to the initial position to return jaw members 110, 120 to the spaced-apart position to release the treated and divided tissue.

Figure 7:
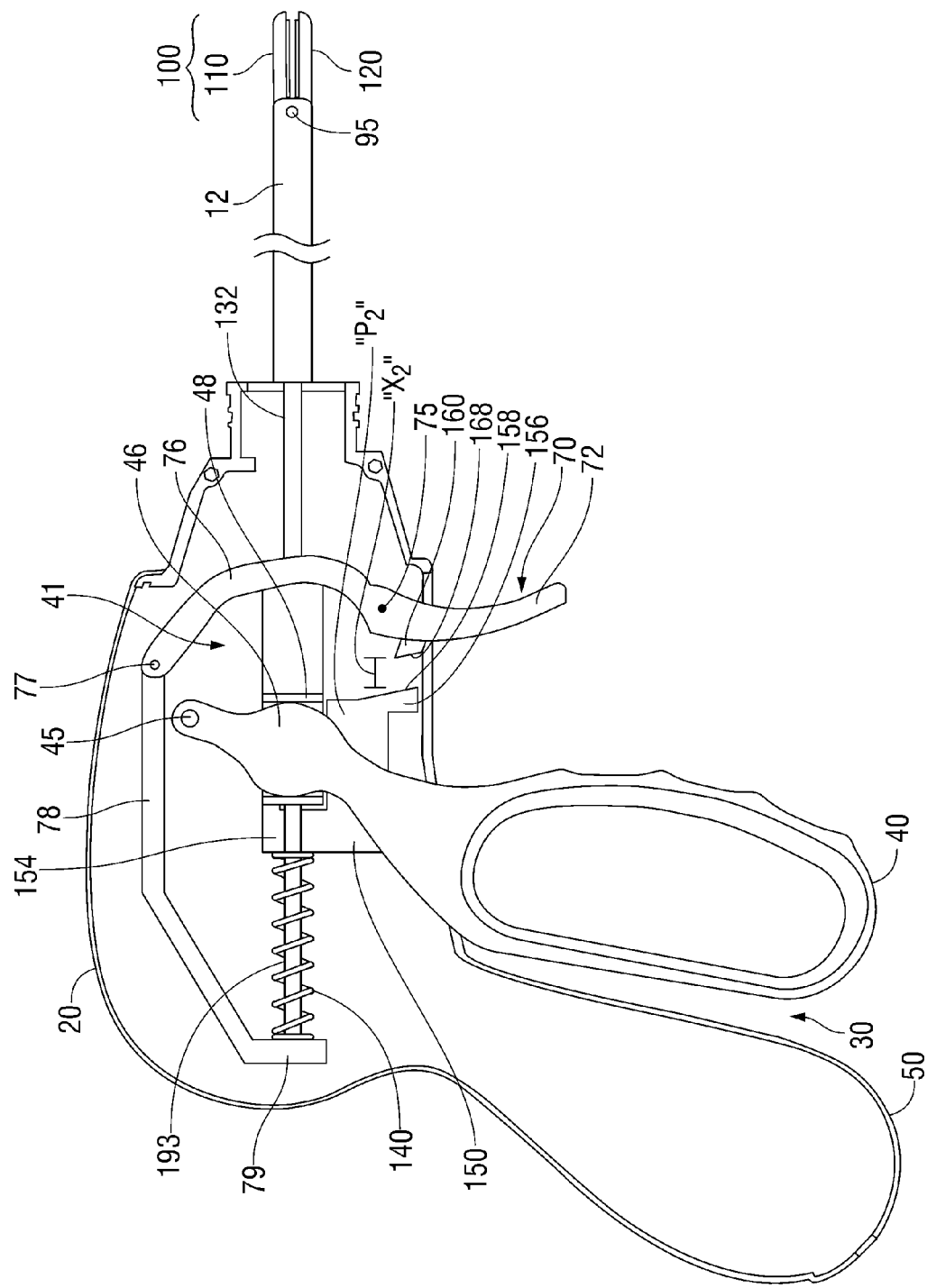
FIG. 7 is a side, cut-away view of the forceps of FIG. 1 wherein the handle assembly is disposed in a second compressed position, the trigger assembly is disposed in an un-actuated position, and the jaw members are disposed in a second approximated position.
Figure 7A:
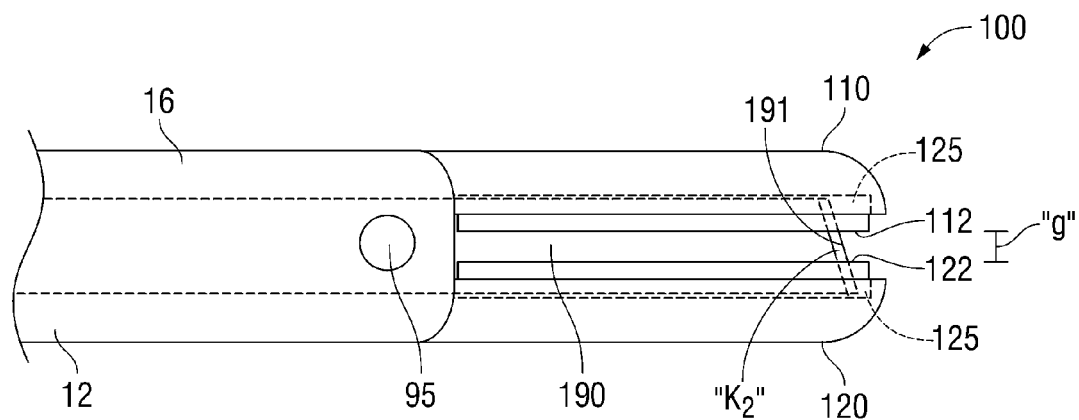
FIG. 7A is a transverse, cross-sectional view of the jaw members of the forceps of FIG. 1 disposed in the second approximated position grasping tissue therebetween, wherein the knife has been advanced between the jaw members to cut tissue grasped therebetween.
Figure 7B:
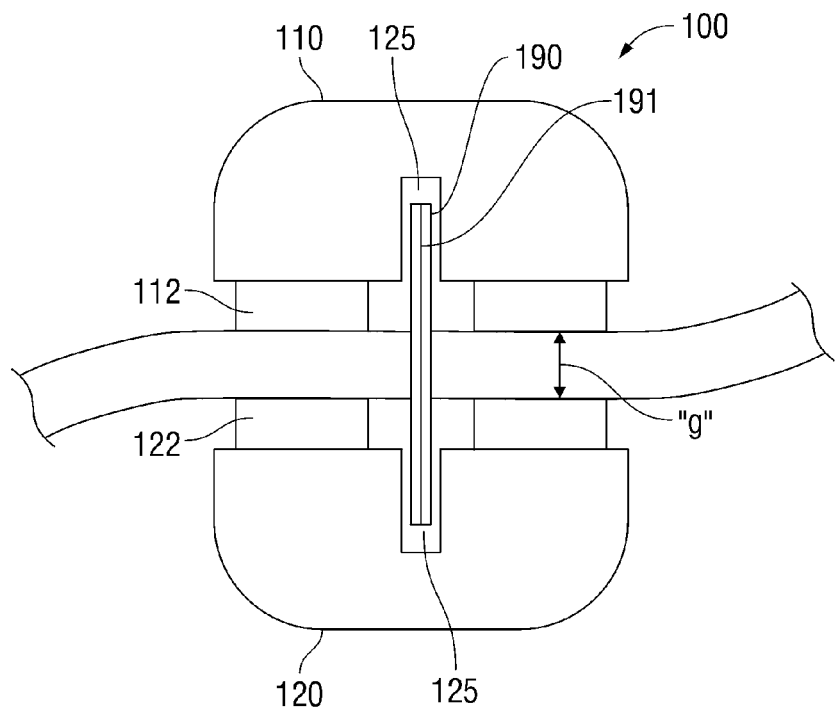
FIG. 7B is a side view of the jaw members of the forceps of FIG. 1 disposed in the second approximated position and including the knife extending therebetween.

Turning now to FIGS. 7 and 7A-7B, in conjunction with FIGS. 1-4B, the use and operation of forceps 10 for grasping, treating, and/or dividing relatively small-diameter tissue, relatively more compressible tissue, for procedures where a smaller gap distance is desired, and/or for procedures where a greater closure pressure is desired, is substantially similar to that described above with respect to FIGS. 6 and 6A-6B and, thus, only the differences therebetween will be described in detail while similarities will be only summarily described or omitted entirely for purposes of brevity.

Initially, to grasp tissue, movable handle 40 is compressed towards fixed handle 50 from the initial position, past the first compressed position, to a second compressed position such that jaw members 110, 120 are pivoted relative to one another to the second approximated position to grasp tissue therebetween and define a relatively smaller gap distance "g" therebetween. Movement of movable handle 40 to the second compressed position effects proximal translation of mandrel 48 and drive sleeve 132 to approximate jaw members 110, 120 and also effects proximal translation of first control member 150 from the initial position "$P_0$," past the first proximal position "$P_1$" (FIG. 6), to a second proximal position "$P_2$," wherein first control member 150 is spaced-apart from second control member 160 a distance "$x_2$." Thereafter, with tissue grasped between tissue sealing plates 112, 122 of jaw members 110, 120, respectively, energy may be conducted between tissue sealing plates 112, 122 and through tissue to treat, e.g., seal, tissue.

At the completion of tissue treatment, or where it is only desired to cut tissue, trigger 72 may be actuated to cut tissue grasped between jaw members 110, 120. Since first control member 150 is disposed in the second proximal position "$P_2$" a distance "$x_2$" from second control member 160, trigger 72 may be actuated further as compared to when jaw members 110, 120 are further spaced-apart. That is, trigger 72 may be actuated from the un-actuated position, past the first actuated position, to a second actuated position, wherein second control member 160 is moved the distance "$x_2$" until complementary angled surface 168 of second control member 160 contacts angled surface 158 of first control member 150 to prevent further actuation of trigger 72. This relatively greater, or further actuation of trigger 72 corresponds to relatively greater distal translation of connector rod 78 and knife drive rod 193 and, thus, relatively further extension of knife 190 between jaw members 110, 120 to position "$k_2$," as shown in FIG. 7B, to cut tissue grasped therebetween.

At this point, knife 190 is prevented from further translation through knife channels 125 and between jaw members 110, 120 due to the abutment of angled surface 158 of first control member 150 and complementary angled surface 168 of second control member 160. However, in this position, knife 190 has been extended further relative to situations wherein jaw members 110, 120 are spaced-apart a greater distance, e.g., as in FIGS. 6 and 6A-6B wherein jaw members 110, 120 define gap distance "G" therebetween, since a relatively greater portion of knife 190 is disposed within and guided by knife channels 125 of jaw members 110, 120, thereby providing greater protection from knife trap, knife splay, and/or knife mis-alignment. Once tissue has been cut, knife 190 is retracted and jaw members 110, 120 are returned to the spaced-apart position to release the treated and divided tissue.

Figure 8:
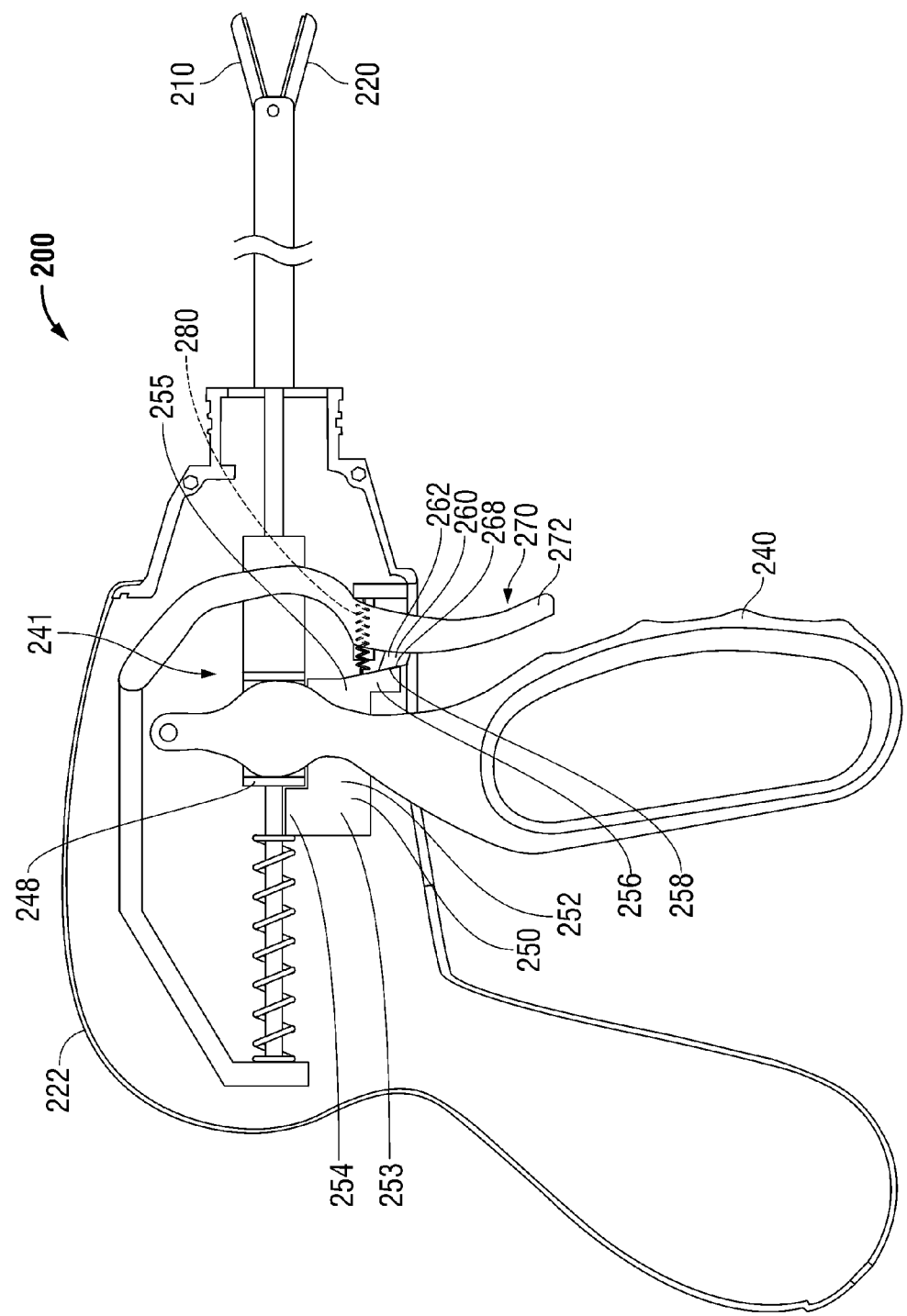
FIG. 8 is a side, cut-away view of another forceps provided in accordance with the present disclosure.

Turning now to FIG. 8, another embodiment of a forceps 200 similar to forceps 10 (FIG. 1) is shown. Forceps 200 is similar to forceps 10 (FIG. 1) except for the configuration and operation of first control member 250 of drive assembly 241 and second control member 260 of trigger assembly 270. Thus, only these differences will be described below to avoid unnecessary repetition.

With continued reference to FIG. 8, drive assembly 241 of forceps 200 includes a first control member 250 and trigger assembly 270 of forceps 200 includes a second control member 260. First control member 250 includes a body 252 defining a proximal end 253 having a proximal finger 254 extending therefrom and a distal end 255 having an engagement leg 256 extending therefrom. Engagement leg 256 of first control member 250, which extends distally from body 252, defines a generally distally-facing angled contact surface 258. First control member 250 is biased distally via a spring 280 coupled between distal end 255 of first control member 250 and housing 222. Proximal finger 254 is positioned adjacent to and proximally of mandrel 248 of drive assembly 241 such that, upon proximal translation of mandrel 248, e.g., upon compression of movable handle 240, mandrel 248 urges first control member 250 proximally. Upon distal translation of mandrel 248, e.g., upon return of movable handle 240, spring 280 biases first control member 250 distally to maintain proximal finger 254 of first control member 250 in abutment with mandrel 248.

Second control member 260, similar to second control member 160 of trigger assembly 70 of forceps 10 (see FIGS. 1-7B), is pivotably engaged to trigger 272. Second control member 260 includes a body 262 defining a generally-proximally facing complementary angled contact surface 268 that is angled similarly to angled contact surface 258 of first control member 250.

In use, first and second control members 250, 260, respectively, of forceps 200 function similar to first and second control members 150, 160, respectively, of forceps 10 (see FIGS. 1-7B). However, rather than preventing actuation of trigger 272 beyond a particular position, first and second control members 250, 260, respectively, provide added resistance and/or feedback, e.g., tactile and/or audible feedback, to the user once trigger 272 has reached the particular position, indicating to the user that the knife 190 (FIG. 3) has been extended to the particular position or is approaching the particular position wherein the knife 190 (FIG. 3) may be vulnerable to knife trap, knife splay, and/or knife misalignment. For example, when movable handle 240 is disposed in the initial position, mandrel 248 is positioned in a more-distal position and, thus, first control member 250 is likewise positioned in a more-distal, or initial position. Further, in this position, jaw members 210, 220 are disposed in the spaced-apart position. In the initial position of first control member 250, angled surface 258 of first control member 250 abuts complementary angled surface 268 of second control member 260. Thus, upon actuation of trigger 272, the user would encounter added resistance in actuating trigger 272 as complementary angled surface 268 contacts angled surface 258 to urge first control member 250 proximally against the bias of spring 280. This added resistance is felt tactilely by the user.

On the other hand, when movable handle 240 is moved to the first compressed position such that jaw members 210, 220 are disposed in the first approximated position, first control member 250 is moved proximally under the urging of mandrel 248 to a first proximal position. In this position, upon actuation of trigger 272, the user would be able to more-freely actuate trigger 272 from the un-actuated position to the first actuated position, but would encounter added resistance upon actuation beyond the first actuated position as complementary angled surface 268 contacts angled surface 258 to urge first control member 250 proximally against the bias of spring 280. Thus, the user would be tactilely alerted as to the extent of deployment of knife 190 (FIG. 3). First and second control members 250, 260, respectively, function similarly with respect to second, third, etc., compressed positions of movable handle 240.

Angled surface 258 and complementary angled surface 268 of first and second control members 250, 260, respectively, may further include teeth, serrations, or other suitable features (not explicitly shown) configured to engage one another upon contact of surfaces 250 and 260, thereby also providing audible feedback to the user. For example, angled teeth would produce "clicking" audible feedback signals as the teeth of surfaces 250, 260 slide in contact with one another upon further actuation of trigger 272 beyond the particular position. The teeth may increase in size, rigidity and/or configuration along the length of surfaces 250, 260 such that a greater audible feedback signal is produced as trigger 272 is actuated further beyond the particular position. Other configurations may also be provided.

Figure 9:
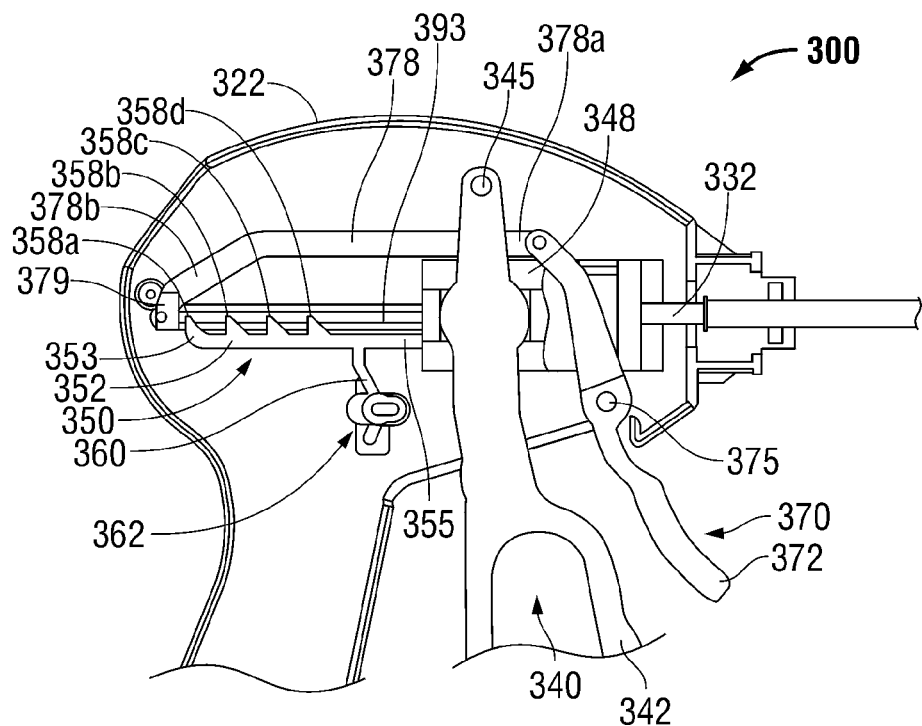
FIG. 9 is a side, cut-away view of another forceps provided in accordance with the present disclosure wherein a handle assembly is disposed in an initial position and wherein a trigger assembly is disposed in an un-actuated position.

Turning now to FIGS. 9-10, another embodiment of a forceps provided in accordance with the present disclosure is shown generally identified by reference numeral 300. Forceps 300 is similar to forceps 10 (FIG. 1) except for the control member 350 thereof. Thus, only these differences will be described in detail below, while similarities will be only summarily described or omitted entirely for purposes of brevity.

Forceps 300 includes a movable handle 340 having a lever 342 pivotably coupled to housing 322 via pivot pin 345 and engaged to mandrel 348 such that pivoting of movable handle 340 between an initial position (FIG. 9) and one or more compressed positions (FIG. 10) translates mandrel 348 and drive sleeve 332 proximally, thereby moving the jaw members 110, 120 (FIGS. 2A-2B) relative to one another from the spaced-apart position (FIG. 2A) to the one or more approximated positions (FIG. 2B). Trigger assembly 370 includes a trigger 372 pivotably coupled to housing 322 via pivot pin 375, a connector rod 378 pivotably coupled to trigger 372 at distal end 378a thereof, and a base 379 coupled to proximal end 378b of connector rod 378 and to knife drive rod 393 such that, upon actuation of trigger 372, connector rod 378 and base 379 are moved to translate knife drive rod 393, to thereby translate knife 190 (FIG. 3) between the retracted position and the one or more extended positions.

Control member 350 of forceps 300 defines an elongated body 352 having a proximal end 353, a distal end 355 that is pivotably or flexibly coupled to mandrel 348, and a plurality of spaced-apart protrusions, e.g., first, second, third and fourth protrusions 358a, 358b, 358c, 358d, respectively, although greater or fewer protrusions may be provided, extending therefrom along at least a portion of the length thereof. Control member 350 further includes an attachment arm 360 extending therefrom that is coupled to housing 322 via a slot-aperture engagement 362, allowing attachment arm 360 and, thus, elongated body 352 to rotate at least partially relative to housing 322 and to translate relative to housing 322 along the length of the slot of slot-aperture engagement 362. As will be described in greater detail below, control member 350 operates so as to regulate the deployment of knife 190 (FIG. 3) as a function of the relative spacing between first and second jaw members 110, 120, respectively (FIGS. 2A-2B), e.g., to prevent deployment of knife 190 (FIG. 3) beyond a particular position that is dependent on the spacing between jaw members 110, 120 (FIGS. 2A-2B) and/or to provide added resistance and tactile and/or audible feedback to the user as to when the knife 190 (FIG. 3) is approaching, has been deployed to, or extends beyond, the particular position.

With reference to FIG. 9, forceps 300 is shown wherein movable handle 340 is disposed in the initial position (such that jaw members 110, 120 (FIGS. 2A-2B) are disposed in the spaced-apart position) and trigger 372 is disposed in the un-actuated position (such that knife 190 (FIG. 3) is disposed in the retracted position). In this position, mandrel 348 is positioned is a more-distal position and, thus, control member 350 is positioned such that first protrusion 358a is positioned distally of and in abutment with base 379. First protrusion 358a (and/or the other protrusions 358b, 358c, 358d) may be formed from a rigid material such that deployment of trigger 372 is prevented in this position or, alternatively, first protrusion 358a (and/or the other protrusions 358b, 358c, 358d) may be formed from a resiliently flexible material such that, in order to actuate trigger 372, the user must provide sufficient force to deflect first protrusion 358a. The resistance to deflection of first protrusion 358a provides added resistance to actuation of trigger 372, thus providing tactile feedback to the user. Teeth or other features (not explicitly shown) on either or both of first protrusion 358a (or any of the other protrusions) and base 379 may be provided for additionally providing audible feedback to the user. As can be appreciated, control member 350, similar to the embodiments above, prevents and/or alerts the user as to when trigger 372 is being actuated, has been actuated, or is attempting to be actuated, when jaw members 110, 120 (FIGS. 2A-2B) are disposed in the spaced-apart position.

Referring to FIG. 10, when movable handle 340 is compressed, or pulled proximally to a compressed position (e.g., a first compressed position, a second compressed position, etc.) to move jaw members 110, 120 (FIGS. 2A-2B) to an approximated position (e.g., a first approximated position, a second approximated position, etc.) to grasp tissue therebetween, mandrel 348 is translated proximally, thus urging control member 350 to rotate and translate in a generally downward direction to the position shown in FIG. 10. The extent of compression of movable handle 340, e.g., whether movable handle 340 is compressed to the first compressed position, the second compressed position, etc., and, thus, the extent of approximation of jaw members 110, 120 (FIGS. 2A-2B), e.g., whether jaw members 110, 120 are moved to the first approximated position, the second approximated position, etc., determines the positioning of control member 350 relative to housing 322 and base 379. As shown in FIG. 10, control member 350 has been moved, e.g., to a second compressed position, such that first and second protrusions 358a, 358b, respectively, no longer interfere with base 379. Thus, trigger 372 may be actuated to translate base 379 and knife drive rod 393 distally, thereby extending knife 190 (FIG. 3) between jaw members 110, 120 (FIGS. 2A-2B), e.g., to a second extended position, until base 379 contacts third protrusion 358c. Thereafter, trigger 372 may be prevented from further actuation due to the interference between third protrusion 358c and base 379 (in embodiments where third protrusion 358c is rigid) or, alternatively, tactile and/or audible feedback may be provided and the user may be required to apply additional force to further actuate trigger 372 (in embodiments where third protrusion 358c is resiliently flexible). As can be appreciated, the spacing of protrusions 358a, 358b, 358c, 358d and/or configuration of control member 350 may otherwise be configured so as to control deployment of knife 190 (FIG. 3) in accordance with the gap distance between jaw members 110, 120, as desired.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a drive assembly movable between a first position and a second position;
   a trigger assembly movable between an un-actuated position and an actuated position; and
   at least one control member coupled to the drive assembly and movable relative to the trigger assembly, in response to movement of the drive assembly between the first position and the second position, between a blocking position and an unblocking position, the at least one control member configured to limit a range of motion of the trigger assembly between the un-actuated position and the actuated position in accordance with a position of the at least one control member relative to the blocking position and the unblocking position.

2. The surgical instrument according to claim 1, wherein the at least one control member continuously limits the range of motion of the trigger assembly between the un-actuated position and the actuated position in proportion to the position of the at least one control member relative to the blocking position and the unblocking position.

3. The surgical instrument according to claim 1, wherein the at least one control member incrementally limits the range of motion of the trigger assembly between the un-actuated position and the actuated position in accordance with an incremental position of the at least one control member relative to the blocking position and the unblocking position.

4. The surgical instrument according to claim 1, further including a handle assembly having a movable handle and a fixed handle, the movable handle operably coupled to the drive assembly and movable relative to the fixed handle between an initial position and a compressed position to move the drive assembly between the first position and the second position.

5. The surgical instrument according to claim 1, wherein the at least one control member is slidable between the blocking position and the unblocking position.

6. The surgical instrument according to claim 1, wherein the at least one control member is pivotable between the blocking position and the unblocking position.

7. The surgical instrument according to claim 1, further including an end effector assembly including first and second jaw members, the drive assembly operably coupled to the end effector assembly such that movement of the drive assembly between the first position and the second position moves at least one of the first or second jaw members relative to the other between a spaced-apart position and an approximated position.

8. The surgical instrument according to claim 7, further including a knife operably coupled to the trigger assembly, the knife movable between a retracted position and an extended position, wherein the knife extends at least partially between the first and second jaw members, in response to movement of the trigger assembly between the un-actuated position and the actuated position.

9. The surgical instrument according to claim 1, wherein the trigger assembly includes a movable trigger, and wherein the at least one control member is configured to block movement of the movable trigger to limit the range of motion of the trigger assembly between the un-actuated position and the actuated position.

10. The surgical instrument according to claim 1, wherein the trigger assembly includes a movable trigger, a base, and a linkage operably coupled between the movable trigger and the base, and wherein the at least one control member is configured to block movement of the base to limit the range of motion of the trigger assembly between the un-actuated position and the actuated position.

11. A surgical instrument, comprising:
   an end effector assembly including first and second jaw members, at least one of the first or second jaw members movable relative to the other between a spaced-apart position and an approximated position;
   a drive assembly operably coupled to the end effector assembly and movable between a first position and a second position to move the at least one of the first or second jaw members between the spaced-apart position and the approximated position;
   a knife movable between a retracted position and an extended position, wherein the knife extends at least partially between the first and second jaw members;
   a trigger assembly operably coupled to the knife and movable between an un-actuated position and an actuated position to move the knife between the retracted position and the extended position; and
   at least one control member coupled to the drive assembly and movable relative to the trigger assembly, in response to movement of the drive assembly between the first position and the second position, between a blocking position and an unblocking position, the at least one control member configured to limit a range of motion of the trigger assembly between the un-actuated position and the actuated position in accordance with a position of the at least one control member relative to the blocking position and the unblocking position.

12. The surgical instrument according to claim 11, wherein the at least one control member continuously limits the range of motion of the trigger assembly between the un-actuated position and the actuated position in proportion to the position of the at least one control member relative to the blocking position and the unblocking position.

13. The surgical instrument according to claim 11, wherein the at least one control member incrementally limits the range of motion of the trigger assembly between the un-actuated position and the actuated position in accordance with an incremental position of the at least one control member relative to the blocking position and the unblocking position.

14. The surgical instrument according to claim 11, further including a handle assembly having a movable handle and a fixed handle, the movable handle operably coupled to the drive assembly and movable relative to the fixed handle between an initial position and a compressed position to move the drive assembly between the first position and the second position.

15. The surgical instrument according to claim 11, wherein the at least one control member is slidable between the blocking position and the unblocking position.

16. The surgical instrument according to claim 11, wherein the at least one control member is pivotable between the blocking position and the unblocking position.

17. The surgical instrument according to claim 11, wherein the trigger assembly includes a movable trigger, and wherein the at least one control member is configured to block movement of the movable trigger to limit the range of motion of the trigger assembly between the un-actuated position and the actuated position.

18. The surgical instrument according to claim 11, wherein the trigger assembly includes a movable trigger, a base engaged to the knife, and a linkage operably coupled between the movable trigger and the base, and wherein the at least one control member is configured to block movement of the base to limit the range of motion of the trigger assembly between the un-actuated position and the actuated position.

* * * * *